(12) United States Patent
Jansson (10) Patent No.: US 8,216,204 B2
(45) Date of Patent: Jul. 10, 2012

(54) SIDE PANEL FOR AN ABSORBENT ARTICLE, SUCH AS A DIAPER, AN INCONTINENCE GUARD OR SIMILAR ITEM

(75) Inventor: Filip Jansson, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 892 days.

(21) Appl. No.: 12/097,365

(22) PCT Filed: Dec. 21, 2005

(86) PCT No.: PCT/SE2005/002008
§ 371 (c)(1),
(2), (4) Date: Jun. 13, 2008

(87) PCT Pub. No.: WO2007/073255
PCT Pub. Date: Jun. 28, 2007

(65) Prior Publication Data
US 2008/0294137 A1    Nov. 27, 2008

(51) Int. Cl.
*A61F 13/15* (2006.01)

(52) U.S. Cl. ......... 604/385.24; 604/385.25; 604/385.26; 604/385.27

(58) Field of Classification Search ............. 604/385.24, 604/385.25, 385.26, 385.27
See application file for complete search history.

(56) References Cited

U.S. PATENT DOCUMENTS

| 5,032,122 | A | 7/1991 | Noel et al. |
|---|---|---|---|
| 5,318,741 | A | 6/1994 | Thomas |
| 5,370,634 | A | 12/1994 | Ando et al. |
| 5,611,791 | A | 3/1997 | Gorman et al. |
| 5,830,298 | A | 11/1998 | Jackson |
| 5,939,467 | A | 8/1999 | Wnuk et al. |
| 6,004,306 | A | 12/1999 | Robles et al. |
| 2002/0058922 | A1* | 5/2002 | Skog .............................. 604/389 |
| 2002/0193776 | A1 | 12/2002 | Fernfors |
| 2003/0114828 | A1 | 6/2003 | Minato |
| 2005/0131373 | A1 | 6/2005 | Wright et al. |

FOREIGN PATENT DOCUMENTS

EP    0 729 332 B1    9/1996

(Continued)

OTHER PUBLICATIONS

Form PCT/ISA/210 (International Search Report) dated Jul. 11, 2006.
Form PCT/ISA/237 (Written Opinion of the International Searching Authority) dated Jul. 11, 2006.

(Continued)

*Primary Examiner* — Jacqueline F. Stephens
(74) *Attorney, Agent, or Firm* — Buchanan Ingersoll & Rooney PC (57) ABSTRACT

An absorbent article, such as a diaper, an incontinence guard or similar, has a front region a rear region and a crotch region located between the front and rear regions. The article includes a central portion with two longitudinal edges and two transverse edges and side panels located in the rear region of the article, placed along the longitudinal edges of the central portion. Each side panel includes a rear portion and a front portion which extend in the transverse direction from the central portion, and the front portion is located at the longitudinal edge of the central portion at a first distance from the transverse edge in the rear region. The rear portion is elastic and the front portion is substantially non-elastic.

12 Claims, 6 Drawing Sheets

FOREIGN PATENT DOCUMENTS

| | | |
|---|---|---|
| EP | 0 937 792 A1 | 8/1999 |
| JP | 4-35663 A | 2/1992 |
| WF | WO 02/22065 A1 | 3/2002 |
| WO | WO 94/26222 A1 | 11/1994 |
| WO | WO 96/29038 A1 | 9/1996 |
| WO | WO 97/47265 A1 | 12/1997 |
| WO | WO 00/01339 A1 | 1/2000 |
| WO | WO 03/047488 A1 | 6/2003 |

OTHER PUBLICATIONS

International Preliminary Report on Patentability and Written Opinion of the International Searching Authority (Form PCT/IB/373 and PCT/ISA/237) dated Jun. 24, 2008, issued by the International Bureau of WIPO in the corresponding International Application No. PCT/SE2005/002008.

Supplementary European Search Report dated Mar. 18, 2011, issued in corresponding European Application No. EP 05 82 1847.

* cited by examiner

SIDE PANEL FOR AN ABSORBENT ARTICLE, SUCH AS A DIAPER, AN INCONTINENCE GUARD OR SIMILAR ITEM

TECHNICAL FIELD

The present disclosure concerns a side panel for an absorbent article, such as a diaper, an incontinence guard or similar, wherein the side panel comprises a rear elastic portion and a substantially non-elastic front portion. The absorbent article has a liquid-permeable topsheet, a backsheet and an absorbent body enclosed therebetween. The article further has a front region, a rear region and a crotch region located between the front and rear regions.

BACKGROUND

Conventional absorbent articles of this type usually have a fastening system for fastening the absorbent article around a wearer. The article is provided with so-called side panels which fit tightly around the wearer's body in the area around the wearer's hips, so that the article sits firmly around the wearer's body in a flexible way which provides the wearer with good movement. The side panels can be produced in the same type of material as the remainder of the article, and often form an extension of the backsheet and topsheet material of the article in the article's transverse direction. The disadvantage of this type of traditional side panels is that the side panels often fold when the article is applied to a wearer. Folded side panels give the article a poor fit, which can lead to chafing or skin irritation. To provide a better fit, the side panels can be elasticated. An elastic side panel has the disadvantage that is it expensive compared to the traditional type of side panels, as well as being harder to optimise from a material point of view so that a good fit is obtained. Another disadvantage is that traditional elastic side panels sometimes do not cooperate with other elastic elements in the absorbent article in an effective way. Examples of elastic side panels are given in WO 03/047488 and EP 0 729 332.

OBJECTS AND SUMMARY

An aim of the present invention is to address the above-mentioned problems and to provide an absorbent article with a side panel which has a relatively low, material and production cost and which simultaneously allows the article to sit stably on the user and which also feels soft and comfortable against the body of the person using the article.

An absorbent article comprises a diaper, an incontinence guard or similar, wherein the article has a front region, a rear region and a crotch region located between the front and rear regions. The article comprises a central portion with two longitudinal edges and two transverse edges. Side panels are located in the rear region of the article, placed on each side of the central portion, along the longitudinal edges of the central portion. Each side panel comprises a rear portion and a front portion which extend in the transverse direction from the central portion. The front portion of the side panel is located at the longitudinal edge of the central portion at a first distance from the transverse edge in the rear region. The rear portion of the side panel is elastic and the front portion is substantially non-elastic.

An absorbent article of the type mentioned in the introduction has been provided which article substantially avoids the previously-discussed problems.

The absorbent article is intended to enclose the lower portion of the wearer's torso like a pair of absorbent pants. It has a front region intended to face forward on the wearer when in use, a rear region intended to face rearward on the wearer when in use, and a narrower crotch region located between the front and rear region, which is intended to be placed in the wearer's crotch between their legs.

The absorbent article comprises a diaper or a incontinence guard comprising a central portion which has two longitudinal edges and two transverse edges. The side panels are located in the rear region of the article, so that they are arranged on respective sides of the central portion in the transverse direction, along the longitudinal edges of the central portion. The central portion comprises a liquid permeable topsheet, a backsheet material and an absorbent body enclosed therebetween. To obtain stable securement of the article on the wearer, the side panels should cooperate with the other components of the absorbent article which contribute to a good fit. Therefore, the side panels comprise a rear portion and a front portion which extend in the transverse direction from the central portion. In this way, the rear portion can cooperate with the rear region of the article to obtain a good fit around the waist of the wearer and the front portion can cooperate with elastic elements in the crotch region of the article. In order that the rear and front portions of the side panels do not fold in the region around the hips of the wearer, the front portion is located at a first distance from the transverse edge in the rear region at the longitudinal edges of the central portion. It is also important that the article does not sit too tightly around the wearer's waist and also offers the wearer flexibility and pliability when the article is placed on the wearer's body. Therefore, the rear portion of the side panel is made of an elastic material. However, the front portion of the side panel should ensure a good, secure fit, as well as cooperate effectively with those elastic elements which are located in the crotch region of the article. This is achieved by the front portion of the side panels being substantially non-elastic.

At least one fastening tab is arranged on the front or rear portion of the absorbent article, for securing the absorbent article around the waist of the wearer. The fastening tab is intended to connect the rear and front regions of the absorbent article to each other by a fastening element arranged on the fastening tab being fastened against a reception portion for the fastening element which is arranged on the front or rear portion of the absorbent article. According to a suitable embodiment, the article is provided with two fastening tabs arranged at the rear side panels of the article, one fastening tab on each rear side panel, and a reception portion on the front region of the article. The reception portion is suitably in the form of a strip, which extends in the transverse direction, parallel with or substantially parallel with the front end edge of the diaper, along a relatively large portion of the transverse edge in the front region. The reception portion comprises a material which is adapted to cooperate with the fastening element. Preferably, the reception portion comprises the female (loop) element of a hook and loop-type fastener, and the fastening element comprises the male (hook) element of a hook- and loop-type fastener. The male and female elements of the hook- and loop-type fastener are usually constituted of a carrier material and a material arranged on the carrier material which either forms hoops or loops and catches or hooks, respectively.

When the article is correctly suited to the wearer, i.e. when the wearer wears an article of the correct size, it should be shaped so that it sits stably about the body of the wearer. To obtain stable fastening of the article, the fastening element of the fastening tabs should fasten against the reception portion so that the fastening system cooperates with other components of the article in the most suitable way.

BRIEF DESCRIPTION OF THE DRAWINGS

In the following, the embodiments of the invention will be described in more detail with reference to the embodiments shown in the drawings.

DETAILED DESCRIPTION OF THE PREFERRED EMBODIMENTS

Figure 1:
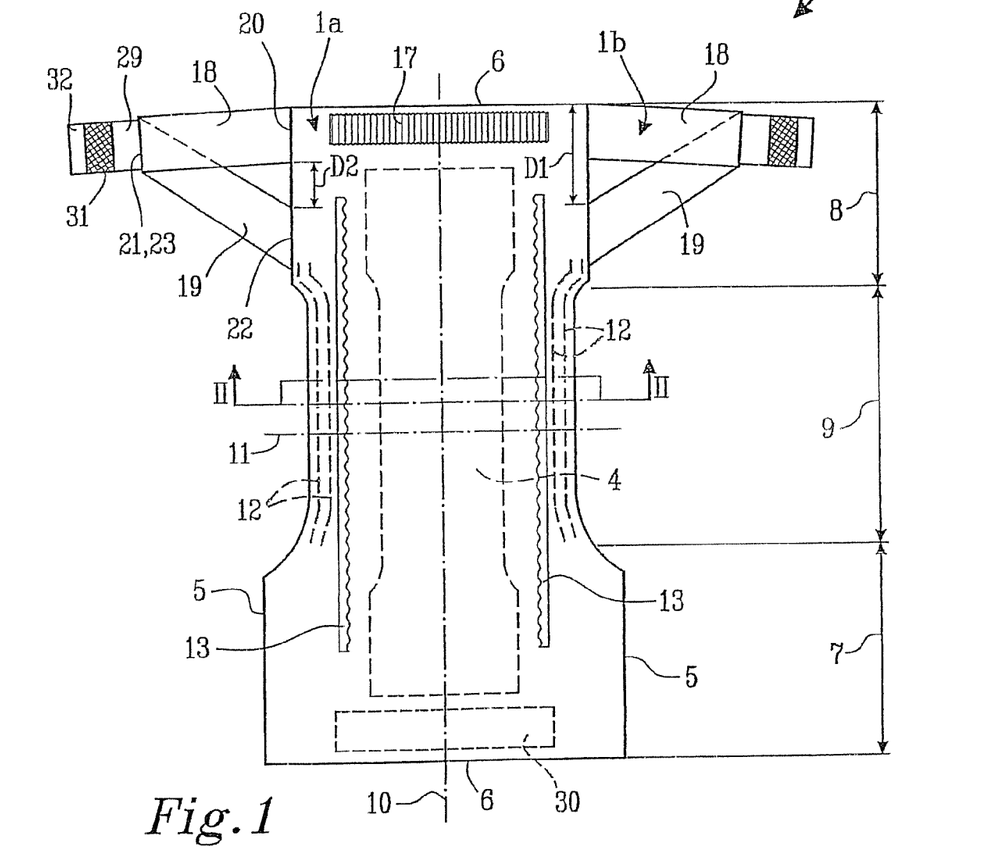
FIG. 1 shows a diaper according to one embodiment of the invention seen from above.
Figure 2:
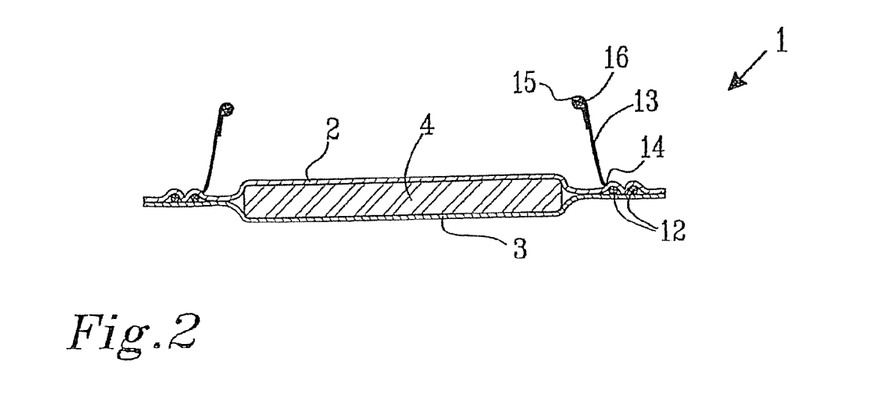
FIG. 2 shows a cross-region along line II-II through the diaper in FIG. 1.

The absorbent article shown in FIGS. 1-2 comprises a diaper or an incontinence guard 1. When in use, the diaper is intended to enclose the lower part of the wearer's trunk like a pair of absorbent pants. The diaper has a central portion 1a which comprises a liquid permeable topsheet 2, a backsheet 3 and an absorbent body 4 enclosed therebetween. The central portion comprises two longitudinal edges 5 and two transverse edges 6. The diaper has a front region 7 intended to face forward on the wearer when in use, a rear region 8 intended to face rearward on the wearer when in use, and a crotch region 9 located between the front and rear region, which is intended to be placed in the wearer's crotch between their legs. The diaper also comprises side panels 1 b arranged on in the rear region, which are located along the longitudinal side edges 5 of the central portion.

Figure 3:
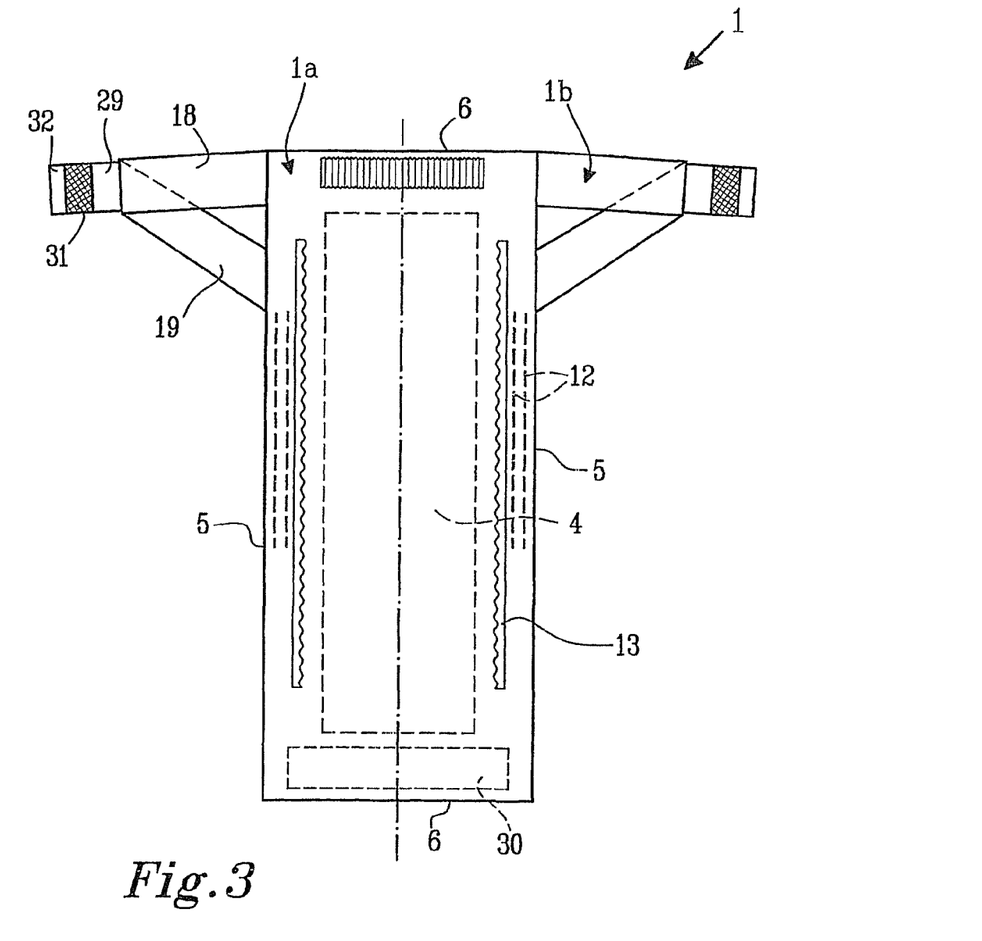
FIGS. 3 and 4 show different embodiments of diapers according to the invention seen from above.
Figure 4:
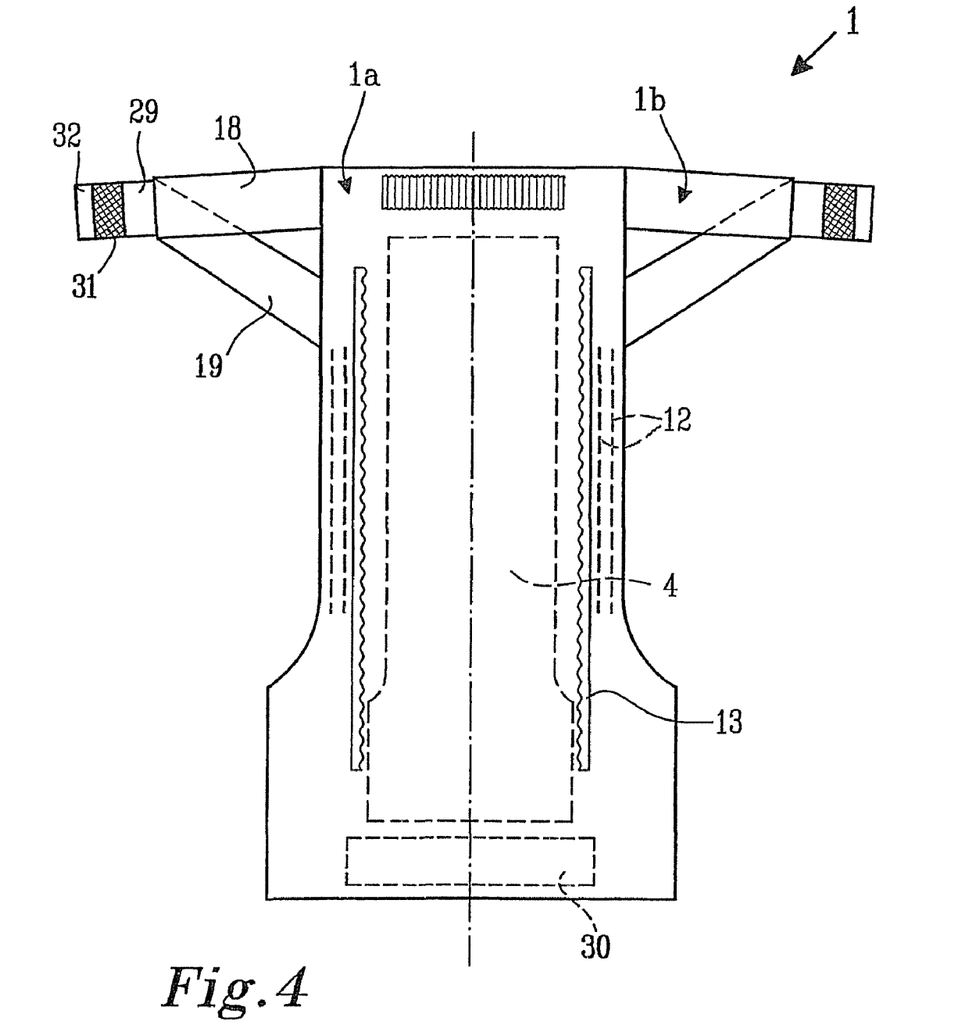

As shown in FIG. 1, the central portion 1a has a form which is elongated in the longitudinal direction. The central portion 1a shown in FIG. 1 is hourglass shaped, with a width in the transverse direction which is larger in the front region 7 and the rear region 8 than in the crotch region 9. The hourglass shape gives the diaper a good fit, which makes it fit tightly round the wearer in a suitable way. The central portion 1a can also for example be rectangular, see FIG. 3, or T-shaped, see FIG. 4. A rectangular central portion has longitudinal edges 5 which are substantially parallel with each other and transverse edges 6 which are substantially parallel with each other. A rectangular shape has the advantage that it is simple to manufacture and also relatively cheap, as unnecessary waste of material can be avoided upon manufacture when the constituent material can be suited to the width of the central portion in the transverse direction. A T-shaped central portion 1a is wider in the front region 7 in the transverse direction than in the crotch and rear regions 9, 8, see FIG. 4. The T-shape has the advantage that it provides the diaper with a shape which has a comfortable and stable fit, in which the front region 7 fits tightly in a comfortable way around the wearer in the area around the wearer's waist, with a greater width in the front region 7 than is the case for a rectangular central portion.

The diaper is suitably symmetric with respect to the longitudinal-aligned axis 10 of the diaper. The transverse direction of the diaper is the direction which extends across the article and is parallel, or essentially parallel with a transverse axis 11, which forms a right-angle with the longitudinal axis 10.

The liquid-permeable topsheet 2 preferably consists of a material which exhibits properties such as dryness and softness when the absorbent article is worn, as this sheet lies against the body of the wearer. It is desirable that the sheet has a soft and textile-like surface which remains dry, even upon repeated wetting. The topsheet can for example be formed from a nonwoven material with a soft and smooth surface such as for example a spunbond of polypropylene fibres, a meltblown material or a bonded carded fibre material. So as to keep the surface closest to the wearer's skin dry, a hydrophobic nonwoven can be used, which has been perforated so that openings are formed in the material which are larger than the space between the fibres in the material. In this way, liquid can be led down through the perforated openings in the topsheet down to the underlying absorption body. Other examples of materials in the topsheet can for example be perforated plastic films, such as e.g. perforated polyethylene film.

The backsheet material 3 is suitably liquid impermeable and can be formed of a thin film of polyethylene (PE), polypropylene (PP) or other suitable material, a hydrophobic nonwoven layer or a laminate of a thin film and a nonwoven material. This type of laminate is often used to obtain a soft and textile-like outer on the backsheet. To provide—a more airy and comfortable article, it is also possible to utilise breathable backsheets which prevent liquid from escaping from the absorbent article but which allow moisture to be ventilated. These breathable backsheets can be made from a single material layer or a laminate of e.g. blown or moulded polyethylene fibres which are laminated with e.g. a nonwoven sheet of spunbond or spunbond-meltblown-spunbond (SMS).

The topsheet 2 and backsheet material 3 have a somewhat greater planar extension than the absorbent body 4 and project outside the edges thereof. Layers 2 and 3 are inwardly bonded within the projecting portions, for example through gluing or welding with heat or ultrasound. They can also be bonded to the absorbent body with e.g. glue.

The absorbent body 4 can be of any conventional type. The absorbent body is usually built up of one or more layers of cellulose fibres, e.g. cellulose fluff pulp. Other materials which can be used are for instance absorbent nonwoven material, foam material, synthetic fibre material or peat. Besides cellulose fibres or other absorbent material, the absorbent body can also contain superabsorbent material, so called SAP (super absorbent polymers), i.e. material in the form of fibres, particles, granules, films or similar, which have the ability to absorb liquid equivalent to several times the weight of the superabsorbent material. The superabsorbent material traps liquid and forms a liquid-containing gel. The absorbent body can further comprise a binder, form-stabilising component or similar. Furthermore, absorbent layers which improve the absorption properties can also be used, such as different types of liquid-distributing material layer or insert, so-called wadding. The absorbent body 4 can be chemically or physically treated to change its absorption properties. It is for example possible to provide an absorbent layer with compressions to control the flow of liquid in the absorbent body. It is also possible to enclose the absorbent layer or absorbent layers in a wrap of e.g. tissue material. The absorbent body 4 usually has a longitudinally extended shape and can for example be essentially rectangular, T-shaped or hour-glass shaped. The absorbent body 4 is suitably adapted to the shape of the central portion 1a, see FIGS. 1, 3 and 4. It is also possible to combine various shapes of the central portion 1a and the absorbent body 4. In a T-shaped absorbent body, the wider portion in the transverse direction is intended to face the front region of the absorbent article in use, so that it lies in the region around the wearer's abdomen in use. An hour-glass shaped absorbent body is wider in the front and rear regions than in the crotch region, so as to provide an effective liquid uptake, at the same time as the design makes it easier for the article to take shape and seal tightly around the wearer.

The portions which project outside the absorbent body on respective sides of the crotch region 9 in the transverse direction are preferably provided with one or more elastic members 12, which extend substantially in the longitudinal direction of the diaper, see FIGS. 1 and 2. The elastic members 12 function as leg elastic and have the role of preventing liquid and faeces from leaking out via the longitudinal edges of the diaper and in this way, form a liquid barrier. The elastic members can comprise one or more elastic threads or strips with are applied in a tensioned state between the backsheet and the topsheet. It is also possible to apply the elastic on the outside of the backsheet or on the inside of the topsheet. The elastic members can also be formed from elastic foam material of e.g. polyurethane foam which is applied between both layers in the same way as the elastic threads.

So as to further hinder liquid or faeces from leaking out, the absorbent article can be provided with inner liquid barriers 13 on the side which faces the wearer, which are fixed in connection with the longitudinal edges, on the inside of the outer liquid barriers, see FIGS. 1 and 2. The inner liquid barriers 13 are preferably formed of a substantially liquid impermeable material such as a hydrophobic nonwoven or a plastic film and are formed as a longitudinal band with a first edge 14 which is connected to the absorbent article and a second free edge 15 which is intended to lie against the wearer when the absorbent article is in use. The second free edge is provided with one or more elastic elements 16, preferably an elastic thread, which in a contracted state pulls the second free edge together so that an upright barrier is formed. The inner barrier can be formed as a strip of a single layer in which the second free edge 15 is folded over so as to enclose the elastic elements and prevent direct contact between the elastic threads and the wearer. Alternatively, the barrier can be formed from two joined layers with the elastic threads fixed between the sheets at the edge of the free edge. The barrier's inner layer can here comprise an extension of the topsheet and the backsheet of substantially liquid permeable material, or the barrier's inner and outer layer can be formed of the same material strip which is wrapped around the elastic threads.

The rear and/or front regions can also be provided with so-called waist elastic 17 which is formed from elastic elements arranged along the transverse edges 6 in the rear region 8 and/or front regions 7 so that the article surrounds the waist of the wearer in a soft and flexible way. The elastic members 17 are suitably fixed between the backsheet material and the topsheet with glue or by welding, e.g. ultrasound welding. The elastic members 17 can comprise one or more elastic threads which are applied in a tensioned state between the layers and thus form waist elastic. Another common type of suitable elastic is elastic foam material comprising a thin strip of e.g. polyurethane foam, which can be applied between both sheets in the same way as the elastic threads. It is of course also possible to place the elastic member of the waist elastic on the outside of the backsheet or on the inside of the topsheet.

As described previously, side panels 1b are located in the rear region 8 and located on respective sides of the central portion 1a along the longitudinal edges 5 of the central portion. The side panels 1 b extend in the transverse direction from the central portion 1a, see FIG. 1, and comprise, according to the invention, a rear portion 18 and a front portion 19 which extend in the transverse direction from the central portion 1a. The extension of the side panels in the transverse direction can be adapted to the central portion 1a on which they are applied, depending on the total width that the article should have in the transverse direction. The extension of the side panels 1b in the longitudinal direction of the diaper can also be adapted in various ways, depending on the diaper on which they are to be used and also on the properties the diaper should have. The purpose of dividing up the side panels 1 b in a rear portion 18 and a front portion 19 is to ensure that the diaper provides a good fit when in use. The diaper should fit securely and comfortably on the wearer's body and also be flexible and comfortable when the wearer moves with the diaper fastened on their body.

Figure 5:
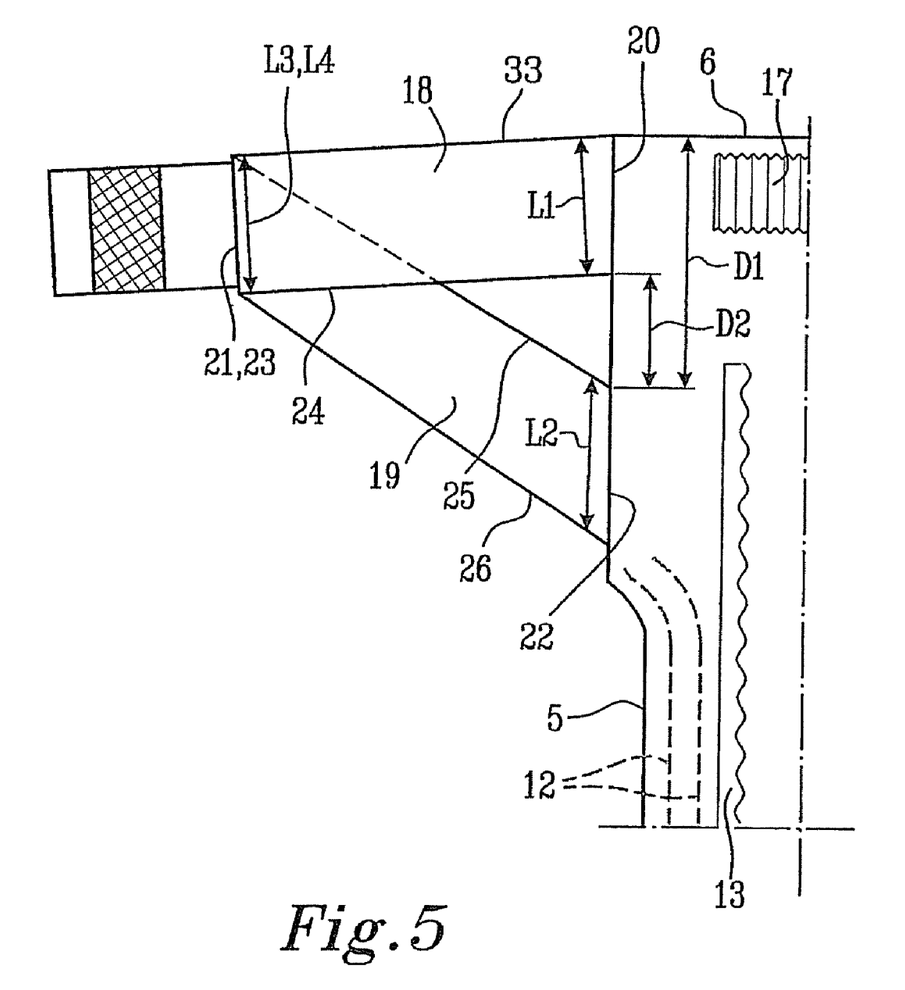
FIG. 5 shows a side panel according to an embodiment of the invention seen from above.

The rear portions 18 of the side panels 1b have proximal edges 20 extending in the longitudinal direction of the diaper, which are bonded to the longitudinal edges 5 in the rear region 8 of the central portion 1a, as well as distal edges 21 which cooperate with distal edges 23 of the front portion 19 of the side panels, see FIGS. 1 and 5. In the same way as for the rear portions 18, the front portions 19 have proximal edges 22 extending in the longitudinal direction, which are connected to the central portion 1a. It should be noted that the longitudinal edges 5 of the central portion do not necessarily have to be parallel with the longitudinal axis 10. In accordance with the invention, they can also extend at an angle to the longitudinal axis, as long as they have an extension from the rear transverse edge 6 of the diaper and forwards towards the crotch region 9. The same also applies to the proximal edges 20, as they are connected to the longitudinal edges 5 in the rear region 8. The extension of the rear portions 18 in the transverse direction can be varied in different ways, depending on the diaper on which they are used. The rear edge 33 and front edges 24 of the rear portions 18 can either be parallel to the transverse axis 11, or extend at an angle to the transverse axle 11, see FIG. 5. The rear edge 33 can either be parallel to the front edges 24 or extend non-parallel with the front edges 24. As the rear portions 18 should cooperate in the most effective way possible with the rear region 8 of the central portion, and any waist elastic 17, it is possible for the person skilled in the art to adjust the portions relative to each other in a number of different ways, within the scope of the invention. The rear portions 18 shown in FIG. 1 have proximal edges 20 and distal edges 21 which extend substantially parallel with the longitudinal axis 10. The rear edges 33 and the front edges 24 are substantially parallel to each other and extend at an angle towards the front region, calculated from the proximal edge 20 to the distal edge 21, in relation to the transverse axis 11.

The rear portions 18 of the side panels 1 b form an extension of the rear portion of the rear region 8 of the central portion in the transverse direction, see FIG. 1, and contribute as previously described to good fit of the diaper around the waist of the wearer. The rear portions 18 cooperate with the material in the rear region 8 of the central portion 1b, so that the material is extended together with the rear portion 18 of the side panel 1b upon applying the diaper to a wearer. The diaper is suitably provided with waist elastic 17 in the rear region 8, as this gives extra good fit on the wearer. In order that the various parts of the rear region of the diaper cooperate in the most effective way, the rear portions 18 of the side panels 1 b are elastic. By "elastic" is meant that the material has properties such that, the material can be extended when subjected to a force, and then substantially return to its original length when the force is no longer applied to the material. In that the rear portions 18 are elastic, they cooperate in an effective way with the waist elastic 17, as well as with the front portions 19 of the side panels 1 b and provide a very secure and comfortable fit around the body of the wearer.

Figure 6A:
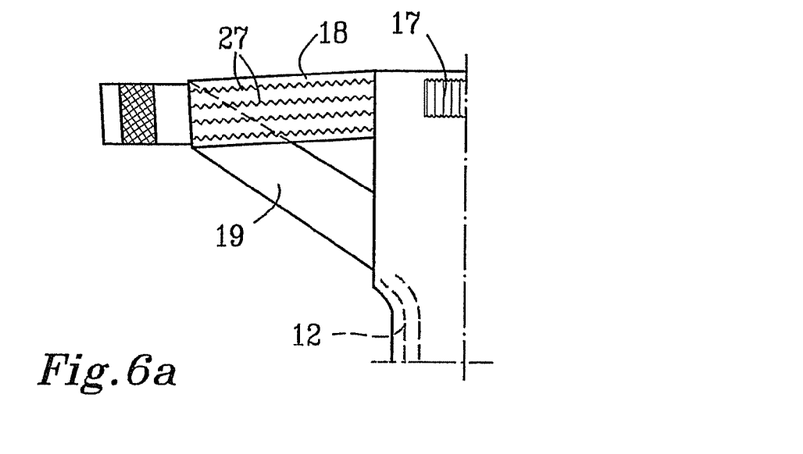
FIGS. 6a-6c show different embodiments of side panels according to the invention seen from above.

The rear portions 18 of the side panels can for example be made of an elastic laminate. The laminate can be formed from different types of two or more materials. A suitable material combination is the use of two layers of nonwoven on either side of an elastic film. Examples of laminates of this type are given in WO 03/047488 and EP 0 729 332. It is also possible to use an elastic film in combination with only one nonwoven layer or more layers of elastic material in combination with one or more nonwoven layers. Another possibility is to use two or more non-elastic materials and provide them with elastic members 27 in the form of threads, bands or foam material, see FIG. 6a. One possible embodiment is to use the same material in the rear portions 18 of the side panels 1 b as in the topsheet 2 and backsheet 3 of the central portion 1a. The extended elastic threads can then for example be applied between the topsheet and the backsheet to endow the rear portions 18 with elastic properties. The elastic threads 27 can be fastened to the surrounding material with glue or by the materials being welded firmly to each other in such a way that the threads 27 are stuck between the material layers. Those parts of the rear portions 18 which face the body of the wearer should be formed from a soft and comfortable material, as this lies against the body of the wearer when the diaper is in use.

Figure 6B:
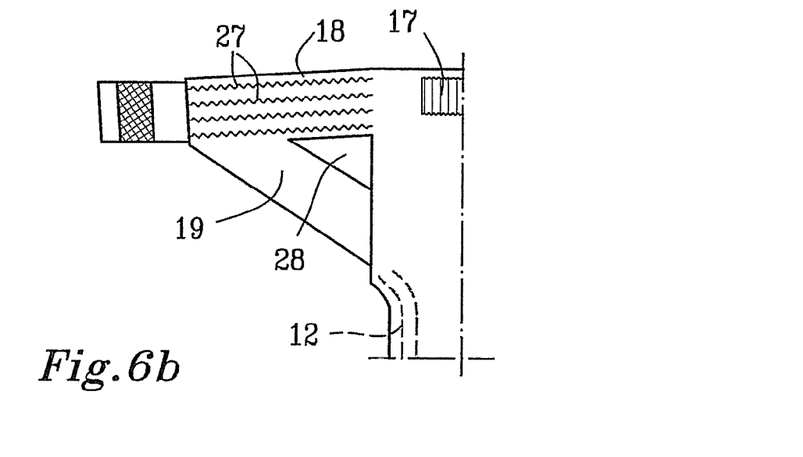

The rear portions 18 of the side panels 1b can be formed of completely separate portions which are fastened to the longitudinal edges 5 in the rear region 8 of the central portion 1a, as well as to the front portions 19, see FIG. 1. If separate portions are used, they can for instance be glued to surrounding parts or fastened with the aid of ultrasound welding or some other sort of thermal fastening. It is also possible to allow the rear portions 18 of the side panels 1b to be manufactured of the same material as the central portion in the area outside the absorbent body 4, see FIG. 6b. According to this embodiment, the rear portions 18 are not formed from separate material pieces but rather instead comprise an extension of the topsheet 2 and the backsheet 3 or only some of the topsheet 2 or backsheet 3 together with some sort of elastic means 27.

The front portions 19 of the side panels 1b have the role of joining the distal edges 21 of the rear portions 18 of the side panels 1b with those portions of the longitudinal edges 5 of the rear region 8 of the central portion 1a which border on the crotch region 9, see FIG. 1. As previously described, leg elastic extends in the crotch region 9, which comprises elastic members 12 and has the function of holding the diaper in position so that it is sealed around the wearer's body. When a diaper is filled with liquid or solid faeces, it is important that it is held up in a secure way, so as to avoid leakage. By ensuring that the elastic means 12 in the crotch region 9 is extended and lies against the wearer's body to the greatest possible extent, a fit is obtained which minimises the risk of leakage. The front portions 19 of the side panels 1 b are therefore formed so that they cooperate with the elastic means 12 in an effective way. When the diaper is fastened on a wearer, the front portions 19 extend the elastic members 12 in the crotch region. So that good extension is obtained, it is important that the front portions 19 are substantially non-elastic, so that a transfer of strain occurs between the proximal edges 22 of the front portions through the elastic members 12 and the distal edges 23 which are connected to the rear portions 18. By "substantially non-elastic material" is meant material which is normally used in this type of absorbent article and which is not provided with elastic members in the form of threads or bands, or alternatively elastic laminates or films in which the elastic properties have been eliminated.

The front portions 19 can for instance be made of nonwoven material or plastic films or combinations of these materials. Another possibility is to use the same type of elastic laminate which is used in the rear portions 18, but in which the elastic has been made ineffective by e.g. thermal treatment, such as ultrasound welding. In the same way as for the rear portions 18, the sides of the front portions 19 which face the wearer's body should be manufactured of a soft and comfortable material.

The front portions 19 of the side panels 1b have proximal edges 22 extending in the longitudinal direction of the diaper, which are attached to the longitudinal edges 5 in the rear region 8 of the central portion 1a, as well as distal edges 23 which coincide with the distal edges 21 of the rear portions 18. The proximal edges 22 can be parallel with the longitudinal axis 10 or extend at an angle to the longitudinal axis, depending on how the longitudinal edges 5 are formed. The extension of the front portions 19 in the transverse direction can be varied in different ways, depending on the diaper on which they are used. The front edges 26 and rear edges 25 of the front portions 19 extend rearwards suitably at an angle relative to the transverse axis 11, as calculated from the proximal edge 22 to the distal edge 23, see FIG. 5. The rear edges 25 can either extend parallel with the front edges 26, or extend non-parallel with the front edges 26. The front portions 19 illustrated in FIG. 1 have proximal edges 22 and distal edges 23 which extend substantially parallel with the longitudinal axis 10. The rear edges 25 and the front edges 26 are substantially parallel to each other.

In the same way as described for the rear portions 18, the front portions 19 of the side panels 1b can be formed of completely separate portions which are fastened to the longitudinal edges 5 in the rear region 8 of the central portion 1a, as well as to the rear portions 18, see FIG. 1. If separate portions are used, they can for instance be glued to surrounding parts or fastened with the aid of ultrasound welding or some other sort of thermal fastening. It is also possible to allow the front portions 19 of the side panels 1 b to be manufactured of the same material as the central portion in the area outside the absorbent body 4, see FIG. 6b. According to this embodiment, the front portions 19 are not formed from separate material pieces but rather instead comprise an extension of the topsheet 2 and the backsheet 3 or only some of the topsheet 2 or backsheet 3. In the embodiment according to FIG. 6b, both the rear portions 18 and the front portions 19 are extensions of the material layers in the central portion 1a. Here, a cut-out 28 has been made in the material to ensure that the elastic rear portions 18 can cooperate with the waist elastic 17 and the substantially non-elastic front portions 19 can cooperate with the elastic member 12 in the crotch region 9.

Figure 6C:
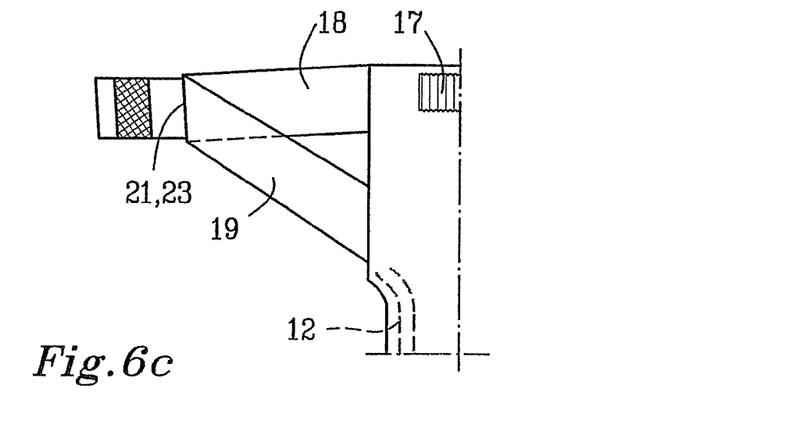

According to a further embodiment, the rear portions 18 and the front portions 19 are made of the same separate piece of material, see FIG. 6c. The piece of material in a side panel 1 b is thus formed of a strip of a suitable material which is folded about the common distal edges 21, 23. The strip can be formed of an inelastic material or laminate in which the rear portion 18 is provided with elastic means. It is also possible to form the strip of e.g. an elastic laminate in which the front portions 19 have been made inelastic as previously described.

In order to ensure that the front portions 19 of the side panels 1b cooperate in the most effective way possible with the elastic means 12 in the crotch region 9, the rear edges 25 are located at a first distance D1 from the transverse edges 6 of the rear region 8, at the longitudinal edges 5 of the central portion, see FIG. 5. The first distance D1 can be varied within the scope of the invention in a number of different ways, depending on which type of diaper they are used on, and depending on the form of the front portions 19. For good cooperation between the various components of the diaper, it is important that the first distance D1 is greater than the distance between the transverse edge 6 in the rear region 8 and the rear edges 33 of the rear portions 18 at the longitudinal edges 5 of the central portion. When the rear portions 18 have rear edges 33 which are arranged such that the first distance D1 is greater than the distance between the transverse edge 6 in the rear region 8 and the rear edges 33 of the rear portions 18 at the longitudinal edges 5 of the central portion, the front portions 19 can cooperate with the elastic means 12 in the crotch region 9 and the rear portions 18 with the waist elastic 17, thus providing good fit of the diaper. For a child diaper of a smaller size, the first distance D1 can be made very short if desired. A smallest suitable length of the first distance D1 for a child's diaper is 15 mm, as the front portions 19 should be able to cooperate with the elastic means in the crotch region without significantly affecting the waist elastic 17. For an, incontinence diaper for adults, the first distance D1 can vary within a very large interval, as there are a number of different sizes and models of diapers on which this type of side panel can be used. Experiments on large types of incontinence diapers have shown that the first distance D1 can have a length of up to 395 mm. This means that the first distance D1 suitably lies within the interval 15-395 mm.

Figure 7A:
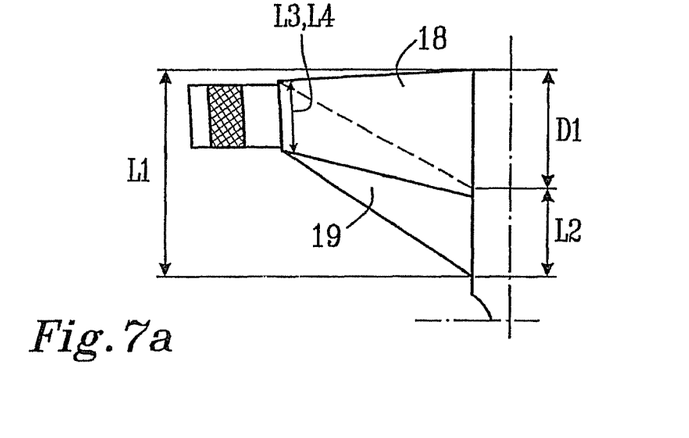
FIGS. 7a-7c show different embodiments of side panels according to the invention seen from above.
Figure 7B:
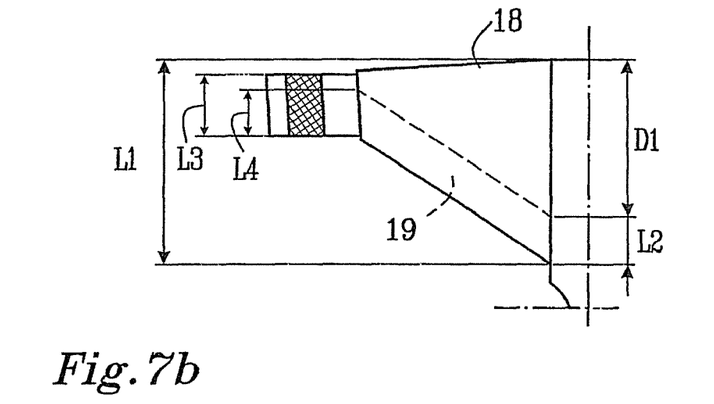
Figure 7C:
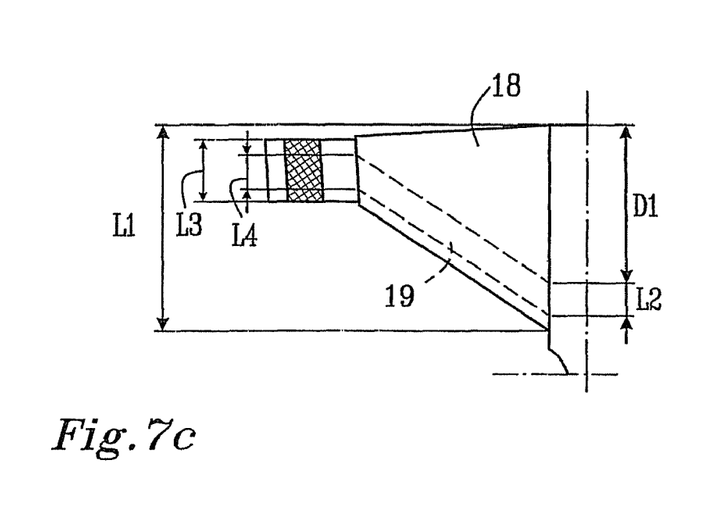

The rear portions 18 have a first length L1 in the longitudinal direction of the diaper at the proximal edges 20 which extend from the transverse edges 6 in the rear region 8 and along the longitudinal edges 5 in the rear region of the central portion 1a in the direction of the front region, see FIG. 5. The front portions 19 have a second length L2 in the longitudinal direction at the proximal edges 22 which begins at the first distance D1 from the transverse edges 6 in the rear region and extends forwards along the longitudinal edges 5 in the rear region, see FIG. 5. The first length L1 of the rear portions can be such that the rear portions 18 do not extend up to the front portions 19 at the longitudinal edges 5, as shown in FIG. 1. According to such an embodiment, the first length L1 of the rear portions 18 is shorter than the first distance D1, and the rear edges 25 of the front portions 19 are located at a second distance D2 from the front edges 24 of the rear portions, see FIGS. 1 and 5. It is also possible to adjust the first length L1 of the rear portions 18 so that they partially or completely overlap the front portions 19 at the proximal edges 20,22, along the longitudinal edges 5 of the central portion. When the rear portions 18 partially overlap the front portions 19, the first length L1 is greater than the first distance D1, but smaller than the sum of the first distance D1 and the second length L2, see FIG. 7a. When the rear portions 18 completely overlap the front portions 19, the first length L1 is as great as or greater than the sum of the first distance D1 and the second length L2, see FIGS. 7b and 7c. The rear portions 18 can overlap the front portions 19 so that the rear portions 18 lie closest to the wearer's body and the front portions 19 lie on the outside of the rear portions. Alternatively, the front portions 19 can be placed on the side which faces the wearer upon use of the diaper and the rear portions 18 outside the front portions 19. Even when the first length L1 is shorter than the first distance D1, the rear portions 18 and the front portions 19 can overlap each other in an area at the distal edges 21, 23, see FIG. 1. It is also possible here to place the rear portions 18 so that the area which overlaps the front portions 19 lies against the wearer's body, or vice versa, that the front portions 19 are arranged so as to lie nearest the body of the wearer in the overlapping area.

The rear portions 18 have a third length L3 in the longitudinal direction of the diaper at the distal edges 21 and the front portions 19 have a fourth length L4 in the longitudinal direction at the distal edges 23. According to the embodiment in FIG. 1, the third and fourth lengths are equally long, but it is possible to allow the third length 3 to be greater than the fourth length L4, see FIGS. 7 and 7c, or vice versa, to allow the fourth length L4 be greater than the third length L3.

The various lengths and distances described above can be adjusted in different ways and can also vary depending on the type of diaper. As this type of side panel is suitable for both baby diapers and incontinence diapers for adults, the length of the first length L1 and the second length L2 can vary within wide intervals. Experiments have shown that the first length L1 should at least be 15 mm, and the second length L2, 5 mm. The first length L1 can be made very large on a larger type of incontinence diaper for adults if so desired, and here it has been shown that the first length L1 can be as large as 400 mm. The second length L2 can suitably be up to 100 mm on a large incontinence diaper. This means that the first length L1 suitably lies within the interval 15-400 mm and that the second length L2 lies within the interval 5-100 mm. The embodiments having the second distance D2 can also be varied in a number of different ways, which leads to that the length of the second distance D2 can be varied by the person skilled in the art in a number of different ways within the scope of the invention. In the same way, the third length L3 and the fourth length L4 can also be varied within the scope of the invention.

It is also possible to use this type of side panels in so-called "belt products". By "belt products" is meant diapers or incontinence guards which have integrated belts or belt segments for fastening the diaper or incontinence guard on the wearer. In a belt product according to the invention, the side panels 1b comprise either the complete belt, or a portion of the belt. Examples of belt products are given in WO 94/26222, WO 02/22065 and US 2002/0193776.

A fastening system for holding the absorbent article around a wearer is arranged on the side panels 1b of the diaper. The fastening system consists of at least one fastening tab 30 29 together with a reception portion 30 for the fastening tab 29. The fastening tab 29 is provided to connect the rear and front regions of the absorbent article to one another, through a fastening means 31 arranged on the fastening tab 29 which is fastened to the reception portion 30 arranged on the front region of the article. Preferably, the article is provided with two fastening tabs arranged on the side panels 1b, one fastening tab on each side panel, as well as a reception portion 30 on the article's front region 7, on the side which faces away from the wearer upon use of the article, i.e. on the outside of the backsheet.

The fastening tabs 29 are bonded to the side panels 1b in the area around the distal edges 21, 23 of the rear portions 18 and the front portions 19, see FIG. 1. Bonding can be achieved by e.g. glue, tape, heat-sealing or welding in discrete points, lines or continuous surface areas. The fastening tabs 29 can be joined to the back side of the side panels, on the same side as the topsheet of the diaper, between the front portions 19 and the rear portions 18 or formed so that the tabs are fastened so that a part of the tab lies on the outside of the side panel and another part of the tab lies on the inside of the side panel, i.e. on the side of the topsheet which faces the wearer.

The fastening means 31 preferably comprises a male portion of a hook and loop fastener. The fastening means 31 is fastened on the fastening tab 29 by e.g. glue, tape, through thermal bonding or with any other suitable fastening agent on the part of the fastening tab 29 which faces the reception portion 30 upon using the diaper. The portion of the fastening tab 29 which is arranged outside the fastening means 31 in the transverse direction can comprise a grip tab 32, which has the role of making application and removal of the fastening means to the reception portion 30 easier.

The reception portion 30 is preferably formed as an extended strip which extends substantially parallel with the transverse edge 6 of the diaper in the front region 7, i.e. in the transverse direction of the diaper, and comprises a material which is designed to cooperate with the fastening means 31. The extension of the reception portion in the transverse direction of the diaper can vary depending on type and size, and can therefore extend over the diaper's entire transverse edge or over a part of it. Suitably, the reception portion extends over a relatively large part of the transverse edge 6 so that a fit of the diaper to the wearer which is as good as possible can be obtained. The extension of the reception portion 30 in the longitudinal direction of the diaper can also vary, depending on how it should be adapted to the diaper, but is suitably adapted to the extension of the fastening means 31 in the same direction. Preferably, the reception portion 30 comprises female portions (loop portions) of a hook and loop fastener and the fastening means 31 comprises male portions (hook portions) of the hook and loop fastener. It should also be possible to use the hook and loop portions the other way round, but loop portions are better suited as the reception portion, as they do not have the same problems as a hook portion, which easily stick to clothing or other material.

The male and female portions of the hook and loop fastener usually consist of a support means and a material arranged on the support means which either comprises loops or hoops, or hook or catches. The manufacture of the reception or fastening means will not be further described in this application, as any suitable way to produce hook and loop fasteners with support means and fastening agent can be used. Suitable material for the reception portion or fastening means can e.g. be polyethene, polypropylene, polyester, polyamide or any other thermoplastic, as well as biologically degradable material such as e.g. polylactide, polycaprolactone or other polyhydroxyalkanoates and materials, e.g. polymeric materials formed from renewable resources, such as e.g. maize starch or cellulose. Examples of ways to produce male or female portions for a fastening means are described more closely in U.S. Pat. No. 5,830,298, U.S. Pat. No. 5,611,791, U.S. Pat. No. 5,032,122, and U.S. Pat. No. 5,318,741 and biologically degradable material in U.S. Pat. No. 5,939,467 and WO 00/01339. Common to the described fastening means and methods for their production is that the hook and loop fastener is built up of a substrate or support portion and that material in the form of hooks or loops is arranged on the substrate.

It is also possible to form the reception portion 30 as a laminate of a nonwoven material or a plastic film and continuous fibres, so-called tow. The fibres can be straight, coiled or curled. Here, the nonwoven layer or plastic film comprises a support means for the continuous fibres. The fibres are bonded to the nonwoven layer so that loops or hoops are formed, which the fastening means 31 can grip. The continuous fibres can be produced separately before being used in the process for manufacturing the reception portion. The fibres are often provided in long fibre bundles or sheaves with a number of fibres arranged alongside one another. Before the fibres are bonded to the nonwoven layer, they should first be separated so that they are arranged in a plane lying substantially parallel to one another so that they can be attached to the nonwoven layer in a suitable manner. This can for instance occur during the manufacturing process in that the fibre bundle is stretched and spread out to a layer of substantially even thickness. Another method can be that a number of fibres, arranged beside one another in a plane, are introduced to the manufacturing process. The continuous fibres are then bonded only in intermittent bonding areas, but are otherwise unbonded. Bonding is obtained through e.g. ultrasound welding or other thermobonding under simultaneous compression. Other possible ways to bind the fibres to the support material can be through bonding agents or mechanical entangling. Suitable materials for the fibres in the tow can be polyethylene, polypropylene, polyamide, polyester, polyvinylacetate, cellulose acetate, regenerated cellulose fibres or bicomponent fibres. An example of handling of tow in manufacturing processes is given for example in EP 0 937 792. One or both of the components comprising the laminate can also be manufactured from a biologically degradable material such as e.g. polylactide, polycaprolactone or other polyhydroxyalkanoate. In this way, a reception portion which is made entirely of a biologically degradable material is suitable for use in an absorbent article which can be composted.

The backsheet 3 can also be manufactured of a material which itself acts as a reception portion for the fastening means 31. The backsheet material 3 can for example have a textile-like surface with fibres which the fastening means can grip, and in such an embodiment, a separate reception portion can be completely eliminated.

The invention should not be considered as being limited to the above embodiments, as these are merely designed to illustrate the invention. It is also possible to combine features from the various embodiments with each other, while remaining within the scope of the invention.

The invention claimed is:

1. An absorbent article having a front region, a rear region and a crotch region located between the front and rear regions, wherein the article comprises a central portion with two longitudinal edges and two transverse edges and side panels located in the rear region of the article along the longitudinal edges of the central portion, wherein each side panel comprises a rear portion and a front portion which extend substantially in the transverse direction from the central portion, and that the front portion is located at the longitudinal edge of the central portion at a first distance from the transverse edge in the rear region, and the rear portion is elastic and the front portion is substantially non-elastic, wherein the rear portion and the front portion of the side panels each have proximal edges which adjoin the rear region of the absorbent article at the terminal edge thereof and the front portion and the rear portion of the side panels each have distal edges, wherein the distal edge of the rear portion of the side panel adjoins the distal edge of the front portion of the side panel.

2. The absorbent article according to claim 1, wherein the rear portions have rear edges which are arranged so that the first distance is greater than a distance between the transverse edges in the rear region and the rear edges of the rear portion at the longitudinal edges.

3. The absorbent article according to claim 1, wherein the rear portions have a first length which extends from the transverse edge of the rear region in a direction towards the front region at the longitudinal edges of the central portion, wherein the first length is smaller than the first distance.

4. The absorbent article according to claim 1, wherein the rear portions have a first length which extends from the transverse edges in the rear region in the direction of the front region at the longitudinal edges of the central portion, and the front portions have a second length which starts at the first distance from the transverse edge in the rear region and extends forward along the longitudinal edges of the central portion, wherein the first length is greater than the first distance, but smaller than the sum of the first distance and the second length.

5. The absorbent article according to claim 1, wherein the rear portions have a first length which extends from the transverse edge in the rear region in the direction of the front region at the side edges of the central portion, and that the front portions have a second length which starts at the first distance from the transverse edge in the rear region and extends forwards along the longitudinal edges of the central portion, wherein the first length is the same size or greater than the sum of the first distance and the second length.

6. The absorbent article according to claim 1, wherein the first distance lies within the interval 15-395 mm.

7. The absorbent article according to claim 1, wherein the first length lies within the interval 15-400 mm.

8. The absorbent article according to claim 1, wherein the second length lies within the interval 5-100 mm.

9. The absorbent article according to claim 1, wherein the rear portions are made of an elastic laminate.

10. The absorbent article according to claim 1, wherein the rear portions are provided with elastic elements in the form of threads, bands or foam material.

11. The absorbent article according to claim 1, wherein the article is a diaper or an incontinence guard.

12. The absorbent article according to claim 1, wherein the distal edge of the rear portion of the side panel and the distal edge of the front portion of the side panel are each attached to a proximal edge of a fastening tab.

* * * * *